United States Patent [19]

Dahl et al.

[11] Patent Number: 5,090,422
[45] Date of Patent: Feb. 25, 1992

[54] IMPLANTABLE ELECTRODE POUCH

[75] Inventors: Roger W. Dahl, Andover; Graydon E. Beatty, New Brighton; David K. Swanson, Roseville; John E. Heil, St. Paul, all of Minn.

[73] Assignee: Cardiac Pacemakers, Inc., St. Paul, Minn.

[21] Appl. No.: 511,068

[22] Filed: Apr. 19, 1990

[51] Int. Cl.⁵ ................................ A61N 1/05
[52] U.S. Cl. .................... 128/784; 128/639; 128/642
[58] Field of Search ............. 128/639, 640, 642, 784

[56] References Cited

U.S. PATENT DOCUMENTS

| | | | |
|---|---|---|---|
| 2,985,172 | 5/1961 | Jones | 128/419 P |
| 4,006,748 | 2/1977 | Schulman | 128/419 P |
| 4,567,900 | 2/1986 | Moore | 128/784 |
| 4,662,377 | 5/1987 | Heilman et al. | 128/419 D |
| 4,860,769 | 8/1989 | Fogarty et al. | 128/786 |
| 4,938,231 | 7/1990 | Milijasevic et al. | 128/784 |
| 4,972,846 | 11/1990 | Owens et al. | 128/784 |

Primary Examiner—William E. Kamm
Assistant Examiner—Scott M. Getzow
Attorney, Agent, or Firm—Haugen and Nikolai

[57] ABSTRACT

A novel method and apparatus for isolating and anchoring an implantable electrically stimulating probe such as a defibrillator patch electrode for use with an automatic cardioverter/defibrillator is disclosed in which a porous bio-compatible coating or enclosure covers and isolates the electrode in a way which allows electrical conductivity via bodily fluid which passes through but separates the electrode from the adjacent tissue in the manner of dissection plane which substantially prevents tissue ingrowth. The coating or enclosure controls the minimum separation distance from the closest tissue and which reduces the local current density applied to adjacent tissue when the electrode is pulsed. The system includes a provision for attaching the enclosure means to internal bodily tissue.

34 Claims, 2 Drawing Sheets

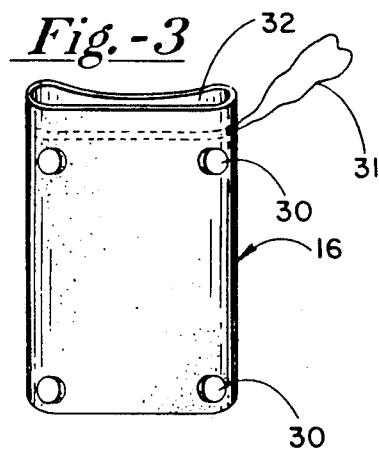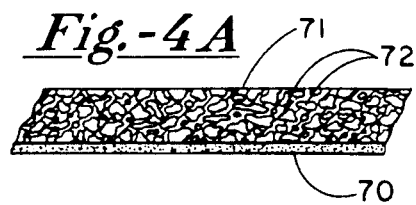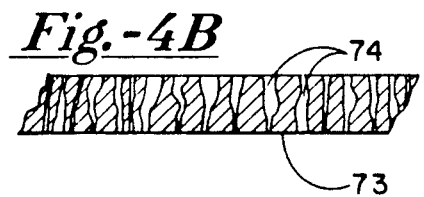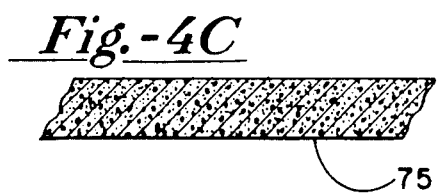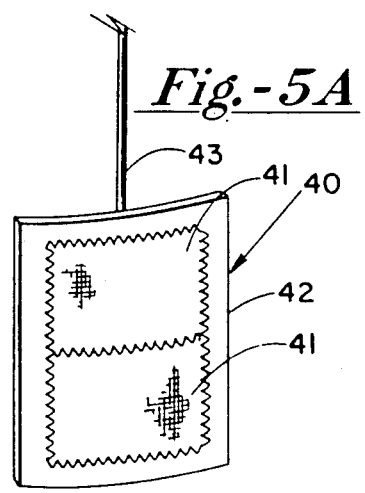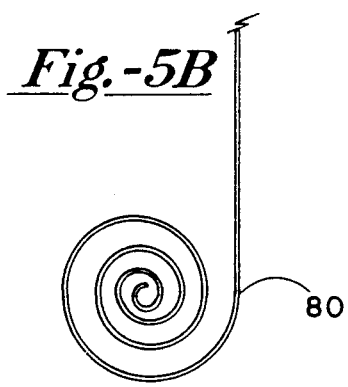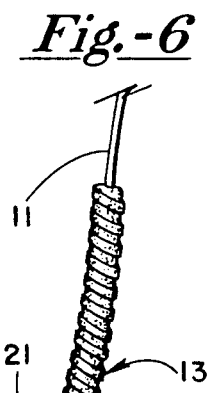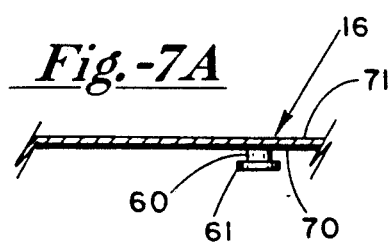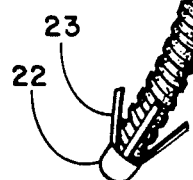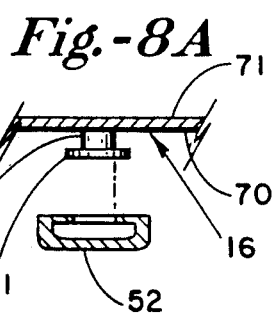

IMPLANTABLE ELECTRODE POUCH

BACKGROUND OF THE INVENTION

1. Field of the Invention

The present invention is directed generally to a novel method and apparatus for isolating and, in some cases, anchoring an implantable electrically stimulating probe such as a defibrillator electrode for use with an automatic implantable cardioverter/defibrillator (AICD). More particularly, it relates to the design of the biocompatible conducting coating or covering or a pouch for containing an electrode which minimizes tissue ingrowth, reduces the current density applied to adjacent tissue, and which, in the case of the pouch, is designed to be fixed to the adjacent tissue in a manner which allows the probe to be inserted and removed using a minimally invasive procedure.

2. Discussion of the Relevant Art

Automatic implantable cardioverter/defibrillator devices have been under development for some time. The term cardioverter is used to mean a device for the correction of either ventricular tachycardia (abnormally rapid heart rate, i.e. 120-180 beats per minute) or ventricular fibrillation (an extremely rapid heart beat disorder) by discharging electrical energy into the heart normally between internally placed electrodes. The electrode arrangement may include a catheter or endocardial electrode which is intravenously positioned within the heart of the patient so that the electrode is within the right ventricle. The other electrode, in the form of a flexible, substantially planar patch, is positioned outside of the heart, either within the thoracic cavity next to the left ventricle, or subcutaneously. The current utilized for the devices is supplied by a battery powered pulse generator implanted under the skin of the patient. Improving the conductance path between the patch electrode and the catheter electrode results in reduced electrical use per defibrillation pulse and this, of course, increases the time that the system can operate without renewal of batteries. Thus, it has also been an advantage to place the defibrillation patch electrode as close to the outer tissue of the left ventricle as possible to shorten the required conduction path.

Placement of the electrode directly on the tissue, however, can result in burns, edema and other tissue injury trauma because of the proximity of the high energy discharge associated with a defibrillation pulse. In addition, tissue adhesion or tissue ingrowth or through growth associated with placement of the electrode directly on the tissue, has resulted in severe removal problems after chronic placement.

As used throughout the specification, the term "dissection plane" is intended to mean any internal boundary which is easily separated even though the adjacent surfaces may be touching. This includes the surfaces of internal organs, for example, which may touch, cooperate and function in harmony but which do not grow together. The term "ingrowth" refers to the cellular penetration of a surface which impedes or hinders its ability to exist as a dissection plane. Specifically, ingrowth refers to cellular penetration of fibrous or connecting tissue through an open or porous surface of a chronically implanted device. The term "adhesion" refers to the surface attachment of fibrils of collagen or the like which can be separated without cutting or incising the tissue.

Previous defibrillation patch electrodes such as those placed on or adjacent to the outer wall of the left ventricle of the heart, have, in some cases, attempted to incorporate an insulating backing material to minimize tissue ingrowth. The insulating layer in the electrode, of course, limits the amount of exposed electrode surface which may result in reduced electrical performance.

Other concepts have been proposed to minimize the invasive nature of defibrillation leads. To date, these approaches have involved incorporation of some form of active fixation device in the lead. Drawbacks of these approaches include limitations on the type of fixation mechanisms that can be used and the necessity that each lead be of a custom design to incorporate its own fixation mechanism. This, of course, complicates the design of the leads. Thus, there remains a definite need to increase the efficiency of implant defibrillation devices while, at the same time, avoiding the problems associated with tissue damage or trauma, tissue ingrowth and the necessity to design complicated fixation mechanisms.

In addition, in order to place the patch electrode on or adjacent to the left ventricle or other desired area of the heart, it has been necessary, with some procedures, for the patient to undergo extensive surgery involving substantial recovery time. The most radical approach involves splitting the sternum or alternatively opening a space between the ribs in order to gain access to the surface of the heart. In a different, less traumatic, surgical approach, a small incision is made from beneath the sternum and the thoracic cavity is entered directly from beneath the rib cage. To date, this approach has not met with a great deal of success, however, because of the limitations of present techniques with respect to proper placement and fixation of the electrodes. Remote manipulation is difficult and a specific mode of attachment designed for remote operation has not been devised.

SUMMARY OF THE INVENTION

By means of the present invention, many of the problems associated with implantation of probes, such as electrodes for use with automatic implantable cardioverter/defibrillators (AICD) are solved by the provision of a unique approach to electrode isolation and attachment. The invention is directed to a technique and a system for long-term, removable attachment in vivo of an invasive electrically active probe structure to internal body tissue which provides an artificial dissection plane interface or surface which prevents the penetration or ingrowth of cells forming an extension or outgrowth of an organ or ingrowth of tissue which might complicate later removal of the probe. This is accomplished without sacrificing electrical conduction; but it is done in a manner which, at the same time, reduces or eliminates harmful tissue trauma associated with the application of electrical energy, as in defibrillation pulses, to or through the proximate issue. The invention, in most cases, allows a simplified surgical procedure for installation and removal of the probes without loss of placement precision or attachment fixation reliability.

The invention involves separating or isolating chronically implanted electrically active devices or probes of interest from the proximate tissue using a material which forms a partial or complete artificial dissection plane with the proximate tissue which reduces or eliminates tissue ingrowth, as desired, without adversely effecting the electrical performance of the device. The material provides a porous barrier which allows the passage of bodily fluids to promote current flow, but which, at the same time, spaces the electrically active device from the proximate tissue to reduce or eliminate tissue trauma associated with repeated electrical discharge. The porous barrier may be in the form of a coating or a pouch or cover and may include integral attachment or fixation devices. The probe/coating or probe/pouch combination may be provided with immobilized anti-biotic or antiarrhythmic medicines or other medications designed for slow release through the membrane to the body.

In one illustrative embodiment, the invention is directed to a device for enveloping or encasing the patch electrode internally in a removably attached porous membrane pouch or sheath which is, in turn, attached to the heart or pericardial sac. The pouch is preferably attached to the pericardium by the use of a post and snap or a clip mechanism which secures the pouch in position yet allows it to be detached and removed by remotely operated insertion and removal tools, as necessary. The porous membrane material is preferably characterized by pores just large enough to allow sufficient penetration of bodily fluids to wet the membrane so it will readily conduct electricity and allow the tissue adjacent the pouch to function normally. Yet the pores are small enough such that substantial tissue ingrowth does not occur. The pouch is preferably constructed of a polyurethane foam or other biocompatible, relatively soft polymeric material which can be produced within the desired range of pore sizes. There is a family of such materials which have been used for vascular grafting or wound boundaries which are bio-compatible and would occur to those skilled in the art for a particular application. These include such materials as woven, porous polyurethane and porous polytetrafluoroethylene (PTFE) can be applied if used with a wetting agent or surface modified.

With respect to the pore size of the material, the full range of allowable pore sizes is yet to be understood. It is believed, however, that materials having an average surface pore size less than about 15 to 20 microns insure a dissection plane which precludes significant tissue ingrowth yet allows the penetration or passage of bodily fluids thereby reducing the electrical resistance and minimizing ohmic losses in the system. In this respect, the relative amount of internal open volume or void fraction should be as high as possible. This can be accomplished through an open cell internal structure or with random connecting pores in the nature of foamed plastic materials in a manner well-known to those skilled in the art.

With the design of the invention, and using the pericardial sac as an example, it is contemplated that the surgeon install the pouch through a small incision made beneath the sternum and through a small opening made in the pericardial sac. Using a custom forceps, or the like, the pouch is then deployed in proper configuration with respect to the desired location. Snaps or clips are then used to secure the pouch in place, as by trapping the pericardial sac between the post and the snap. Radiopaque markers can also be incorporated in the pouch to aid in the visualization and final positioning of the patch electrode device. Once the pouch is in place, the electrode can then be inserted possibly in a folded configuration, or extended in the case of a coiled filament, into the pouch through an opening in the lower end thereof, and thereafter opened (or coiled) to its flat disposition. The pouch then being next closed as by a drawstring, zipper, Velcro closures (Velcro is a trademark of Velcro Corp. of New York, N.Y. for hook and loop polymer tape) or the like The procedure can be readily reversed to remove the electrode and/or pouch from the patient.

BRIEF DESCRIPTION OF THE DRAWINGS

In the drawings:

FIG. 3 is a view of a pouch for use in accordance with the invention;

FIGS. 4A, 4B and 4C are enlarged fragmentary cross sections of membrane material for use in the pouches or coatings of the invention;

FIGS. 5A and 5B depict two electrode configurations for use with the pouch of FIG. 3;

FIG. 6 shows the use of a membrane coating embodiment in conjunction with the endocardial and distal tip electrodes adapted for placement in the right ventricle illustrated in FIG. 1; and FIGS. 7A, 7B, 8A and 8B depict illustrative post and snap mechanisms for use with the pouch of the present invention.

DESCRIPTION OF THE PREFERRED EMBODIMENTS

Figure 1:
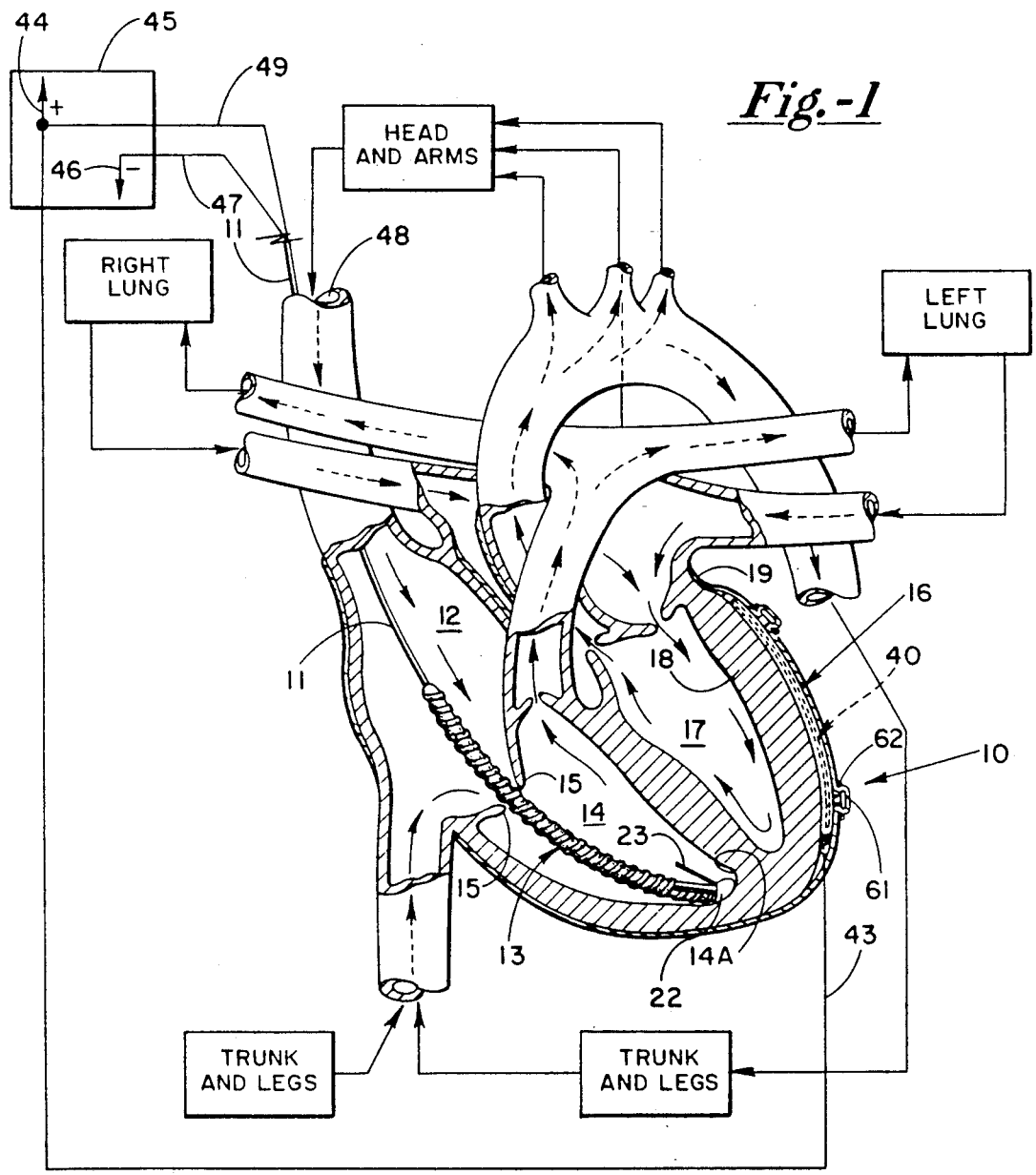
FIG. 1 shows a pouch containing a patch electrode and a coated endocardial electrode of an AICD device in accordance with the present invention installed with respect to a heart.

FIG. 1 depicts a heart shown generally at 10 and fitted with electrodes, as will be described, for an automatic implantable cardioverter/defibrillator (AICD). The endocardial defibrillation lead, as illustrated at 11 extends through the right atrium 14 connecting with an endocardial electrode 13 installed in the right ventricle of the heart 10. The probe is usually installed to extend to the right ventricular apex 14A and is illustrated as extending from there through the tricuspid valve 15.

As better illustrated in FIG. 6, the probe includes a sheathed or coated endocardial electrode member 13 and an exposed distal tip electrode 22. Tissue engaging or fixation barbs are shown at 23 and the porous coating is designated by 21. The electrode is preferably of a helical or spiral shape and is designed to be located close to the tissue structure of the right ventricle. The thin coating membrane 21, in accordance with the present invention, is a bio-compatible porous material which is relatively inert to bodily fluids and has a soft or spongy nature which gives readily upon contact. The material has pores of sufficient size such that the fluid within the heart may penetrate the pores to wet through the membrane coating and has a high enough void fraction to ensure excellent electrical conduction between the electrode and the tissue. The pores are also small enough to create a dissection plane with respect to adjacent tissue.

In FIG. 1, the distal electrode is shown as extending through the tricuspid valve 15 so as to illustrate the worst case location with respect to interfacing with heart tissue. Here the electrode surface and heart tissue interaction includes the repeated impact action of valve tissue against the outer surface of the electrode and the repeated abrasive contact of heart valve tissue rubbing against the outer surface during the opening and closing of the tricuspid valve 15. Contact is also occasioned by the expanding and contracting of the ventricle itself. By coating the electrode with the membrane 21 irritation and injury to the valve and ventricle are greatly reduced because it presents a much softer, more resilient surface to be impacted by the heart tissue.

FIG. 1 also illustrates a patch electrode mounted in accordance with the invention for an AICD system which is proximally positioned as by a pouch member 16 with respect to the outer wall 18 of the left ventricular chamber 17 of the heart. The pericardium is illustrated by 19 and the pouch 16 is normally inserted between the outer surface of the left ventricle and the pericardial sac through a small incision made in the sac, not shown. The pouch 16 itself is better illustrated in FIG. 3 and includes a plurality of post members 30 fixed to the outer side thereof and a closure mechanism illustrated by a drawstring 31 which can be remotely utilized to close the opening 32 in the end portion of the sac after insertion of the patch electrode. The patch electrode itself is illustrated in FIG. 5A and is generally a very flexible conformial mesh which opens to form a thin, generally planer electrode as at 40, having metallic mesh areas as at 41 and is partially encased by a biocompatible polymer material 42 and provided with an electrical lead 43.

The pouch 16 ma be made of a composite version of the thin porous bio-compatible material described with regard to the endocardial electrode, above. The material is described in greater detail below in conjunction with FIGS. 4A-4C. One additional attribute required of the pouch 16, however, is that it be characterized by a pore size suitable to allow penetration of bodily fluids but one small enough such that a dissection plane or interface surface is formed so that tissue ingrowth is properly controlled upon chronic placement in the body.

It should further be noted that an amount of tissue adhesion and, in some cases, even a certain limited amount of ingrowth with respect to long term placement of a probe can be tolerated; and, in some cases, may even be desirable to aid in maintaining the desired placement of the probe. Tissue ingrowth, however, which results in attachment so strong that a incisive surgical procedure is necessary for removal, is not desirable and is important to avoid.

FIGS. 4A, 4B and 4C depict membrane or coating structures in greatly enlarged schematic cross sectional views. FIG. 4A depicts a composite membrane layer in which a relatively thin skin layer 70 is combined with a relatively thick highly porous under layer 71. The relatively thicker highly porous layer 71 provides definition and structural support to the membrane system. The open pored or open celled nature of the highly porous layer does not increase the electrical impedance of the composite. The size of the pores 72 in the layer 70 can be closely controlled and the layer 71 selected to have a high void volume. FIG. 4B depicts a single layer membrane 73 of controlled pore size as at 74 and FIG. 4C depicts a thin coating 75 of controlled porosity.

Materials contemplated include a class of materials compatible with body tissue similar in nature to those used for synthetic vein grafts or wound boundaries (i.e. woven dacron, porous polyurethane or the like). With respect to porosity, the outer pore size compatible with providing the desired dissection plane may vary, it is contemplated that a pore size less than or equal to 20 microns will suffice to prevent unwanted ingrowth. The electrical resistance must be kept as low as possible (approximately 2 ohms) to minimize losses in the electrode system. Thus, both the percentage of open with respect to through pores and the void fraction of the volume should be kept high.

With respect to the thickness of the coating or membrane of the invention, a further important factor to be considered concerns the reduction of undesirable side effects from the relatively high current densities associated with electrical discharges from such probes. Implant defibrillator electrodes placed next to tissue have commonly been known to produce burns, edema and other unwanted effects to adjacent tissue after repeated discharges or pulses. The membrane of the present invention has been found to significantly reduce or even eliminate these undesirable side effects by spacing the active electrical device from the adjacent tissue. It has been found that a total coating or membrane thickness of about 0.010 inches (10 mils) or greater causes a significant decrease in undesirable effects and above a thickness of about 0.080 inches (80 mils) to 0.10 inches (100 mils) such problems are almost non-existent.

The elimination of unwanted local effects produced by high current densities, accordingly, is an important aspect of the present invention in addition to other attributes of the invention which combine to produce a clearly superior implant probe. These improvements represent significant progress. Yet still other benefits exist and are discussed next below.

In accordance with an additional aspect of the present invention, the posts 30 (FIG. 3) present a unique method for mounting the pouch 16 or other such device in the body. Two representative fixation systems involving post and snap designs are illustrated in FIGS. 7A, 7B, 8A and 8B. In FIGS. 7A and 7B, the post member 60 having extended top 61 is designed to engage nitenal clip ring 62 (FIG. 6) much in the fashion of a traditional garter snap of old. In FIGS. 8A and 8B post 50 is shown having an extended top 51 which is designed to engage a button snap member illustrated at 52 in a well-known snap fit manner. The post 50 is shown attached to the membrane of the pouch 16.

Figure 2:
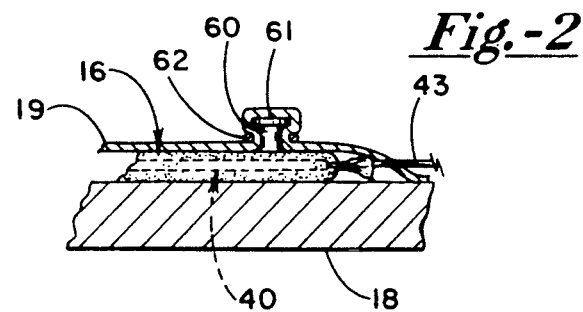
FIG. 2, is an enlarged fragmentary view of a pouch attachment mechanism.

As illustrated once again in FIGS. 1 and 2, the pouch 16 is designed to be inserted inside the pericardial membrane or sac 19 and precisely positioned with respect to the outer wall 18 of the left ventricle 17, being fixed to the pericardial sac by clips such as those illustrated in FIGS. 7A, 7B, 8A and 8B in which the pericardial sac 19 is trapped between the posts 60 attached to the pouch 16 and the closure clip members 62 as illustrated in FIG. 2. Not only does this technique positively position the pouch with respect to the left ventricle portion of the heart, it also accomplishes the positive placement in a manner that allows remote placement and removal, as by installing and removing the clips utilizing special forcep tools, with a minimum of surgical trauma to the thoracic cavity. The whole operation can be done through a small surgical opening beneath the sternum and a small opening in the bottom of the pericardium. The pouch itself is quite flexible and non-abrasive and can be folded and inserted through a very small opening. Once the pouch is secured in place, the patch electrode 40 can then be inserted through the same surgical opening and in through the opening 32 in the lower end of the pouch so that the pouch 16 envelops the electrode 40. The drawstring 31, or other closure device, may then be closed securing the electrode 40 within the pouch 16 such that only the electrode lead 43 protrudes from the pouch. The patch electrode can be readily removed from the pouch simply by using a tool to again expand the opening 32 and reversing the operation of pulling the drawstring 31. Of course, other types of closure mechanisms can be used including zippers, Velcro closures, or the like. The use of snaps, or the like, to position the pouch with respect to the heart enables easy removal of the pouch itself, if necessary, due to the unlikely occurrence of an infection or other problem which might be peculiar to the patient involved.

As discussed above, the pouch is made of a porous material which passes bodily fluids and has a very high percentage of void volume to thereby permit excellent electrical conduction through the membrane from the patch electrode. The material must be chemically compatible with all tissues and bodily fluids contacted during its implantation. It must present a dissection plane or interface boundary to minimize tissue adhesion with respect to mounting a mesh structured object such as the patch electrode in quite close proximity to the tissue of the heart itself. The outer pore size of the membrane material of the pouch 16 is controlled such that the pores contacting the outer wall of the heart are small enough to minimize ingrowth and through growth of tissue during chronic placement. The thickness of the pouch wall spaces the electrode from the adjacent tissue to reduce or eliminate the effects of localized high current densities.

The "post and snap" mechanism technique utilized to secure the pouch to the pericardial sac contemplates hard plastic or metallic materials which are again compatible in all necessary ways with the environment of implantation such that no foreign body reactions occur. The post members, themselves, may be of a firm rubber material and the snaps may be plastic, metal or coated metal. The system, in any case, should be one where engagement and disengagement of the snaps may be made utilizing remotely operated tools so that the pouch may be inserted and removed with a minimum of surgical trauma. Of course, the pouches could be sutured or stapled in place directly to the wall of the heart tissue as an alternative depending on the particular application involved.

With respect to normal installation of the invention, it is envisioned that a small incision would be made to access the thoracic cavity from beneath the sternum and the rib structure and that the surgeon would make a small opening in the pericardial sac. The pouch would be folded up and inserted through that small opening whereupon it would be unfolded, and, using custom forceps or the like, the pouch would be deployed and precisely positioned. Likewise, the electrode may be inserted in a folded form and deployed in the pouch. A planar spiral form of electrode as illustrated at 80 may be inserted in linear form and assume a coil shape upon being released in the pouch in accordance with the invention.

Whereas the above description of the invention has particularly dealt with AICD electrodes, it is by no means meant to limit the scope of the invention. The invention is deemed to extend to any type of chronically implanted stimulating probe or other such device where any of the several advantages would provide useful progress. These include instances wherein a dissection plane or boundary is desired; to prevent or reduce tissue ingrowth, or wherein repeated impact or abrasion may present a problem, or wherein the application requires electrical impedance to be minimal, or wherein current density applied to adjacent tissue needs to be controlled.

Many variations on the theme of the illustrative embodiment are also possible. For example, it is contemplated that the coating disclosed for the endocardial or catheter electrode could be adapted to be used directly on a patch electrode; the catheter electrode could be enclosed in a pouch, etc. Electrodes or probes may take shapes other than those illustrated; and as stated above, may be inserted in configurations other than those assumed upon final deployment.

Special tools would secure the pouch in place by trapping the pericardial sac or other tissues between the post and the snap in the desired position. Radiopaque markers in the pouch could aid in the visualization or precise pouch positioning. Once the pouch was secured in place, the electrode could be inserted through the same openings into the pouch. The draw string or other closure device would then be utilized to secure the patch electrode within the pouch.

In operation, as seen in FIG. 1, the patch electrode 40 is connected via conductor 43 to the anode 44 of a pulse generator 45 and the distal electrode is connected to the cathode terminal 46 via conductor 47. A more proximal electrode (not shown) is normally located at a position within the superior vena cava 48 when the distal tip electrode 22 is at the right ventricle apex 14A. That electrode has a lead 49 commonly connected with lead 43 from patch electrode 40. When the AICD pulse generator detects a life-threatening, abnormal heart rhythm, it is designed to issue a cardioverting or defibrillating pulse across the distal electrode and the combination of the proximal electrode and the patch electrode. This is designed to shock the heart back into its normal rhythm and such implants are associated with patients having a potential for fibrillation.

It will be appreciated that the membrane material of the invention can also be used to solve problems in conjunction with devices such as epicardial electrodes which are implanted routinely as a prophylactic measure during open chest procedures to circumvent the need for subsequent chest procedures. It has been the practice to cap or cover the terminal ends of these devices with silicone rubber boots and leave or store them in a subcutaneous location for possible future connection to an implantable device such as a defibrillator or pacemaker. Scar tissue forms and envelopes these devices making extraction for use difficult and increasing the likelihood of damage to the leads. Once damaged the leads must be replaced.

In this regard membrane material in accordance with the invention can be configured in pouch or any other form or combination of forms which might occur to those skilled in the art as required to control scar tissue interference or interferences associated with other types of tissue growth which might impede the ability to subsequently free the proximal lead ends for use including the uncoiling of such leads from a coiled configuration.

This illustrates that the membrane of the invention also is useful to isolate or substantially isolate long term implants involving devices or parts of devices other than electroactive probes. Coverings or enclosures in accordance with the invention may be tailored to solve specific problems. In certain cases double enclosures such as using a coating on a member within a pouch is possible. The porosity and resilience also may be varied as needed.

The porous nature of the isolating barrier or membrane of the invention provides a still further advantage in that antibiotics, antiarrhythmic or other immobilized drug materials can be incorporated in association with the implantation of a probe device to diffuse or otherwise be made available to the host body over an extended period. This attribute lends itself to the in situ delivery of infection fighting or other materials simultaneously with the implant to further reduce the chance of infection during recovery from the implant trauma.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. In an automatic implantable cardioverter/defibrillator (AICD) system for delivering electrical shocks to the heart of a patient to restore normal cardiac rhythm, the system including an electrical input pulse generating means for generating an electrical pulse in cooperation with at least two implantable electrodes including an endocardial electrode electrically connected to said pulse generating means adapted to be positioned in the right ventricle of the heart of the patient, and a patch electrode electrically connected to said pulse generating means, said patch electrode being adapted to be positioned juxtaposed to the outside of the left ventricle of the heart, the improvement comprising:
    porous bio-compatible enclosure means for isolating said patch electrode in a manner which allows electrical conduction but spaces the patch electrode from the heart tissue so as to achieve a dissection plane, said enclosure means having a thickness which defines a tissue-electrode spacing that reduces proximate tissue damage from high localized current densities, said closure means being further adapted to be fixed in position relative to proximate tissue to thereby positively position said patch electrode in the desired position with respect to the heart; and
    fixation means for attaching said enclosure means proximate to the heart.

2. The automatic implantable cardioverter/defibrillator system of claim 1 wherein said porous bio-compatible enclosure means further comprises a porous polymer membrane pouch including pouch closure means, said pouch having sufficient porosity to allow passage of bodily fluid which promotes electrical conduction, but wherein the average outer pore size is small enough to minimize tissue ingrowth.

3. The automatic implantable cardioverter/defibrillator system of claim 2 wherein said fixation means further comprises a plurality of bio-compatible post members fixed to the outside of said enclosure means and adapted to cooperate with retainers selected from snap and clip members in a manner which fixes said enclosure means to the proximate tissue by trapping it between said post and the selected snap or clip retainer member.

4. The automatic implantable cardioverter/defibrillator system of claim 1 where the outer pore size is less than or equal to 20 microns.

5. The automatic implantable cardioverter/defibrillator system of claim 4 wherein the thickness of said enclosure means is between about 10 mils and 100 mils.

6. The automatic implantable cardioverter/defibrillator system of claim 1 wherein said fixation means comprises post and retainer arrangements.

7. The automatic implantable cardioverter/defibrillator system of claim 1 further comprising a coating of a porous biocompatible material covering said endocardial electrode, said coating being of sufficient porosity to allow ingress of bodily fluids to enable electrical conduction through said enclosure, said coating having a thickness which defines the tissue-electrode spacing required to reduce the localized correct density of the generated pulse applied to the tissue to a desired atraumatic level, said coating further being of a soft, resilient non-abrasive material reducing the effect of repeated impact and rubbing between said endocardial electrode and the heart tissue.

8. The automatic implantable cardioverter/defibrillator system of claim 7 further comprising an amount of medication immobilized in at least one of said enclosure means and said coating material.

9. The automatic implantable cardioverter/defibrillator of claim 7 wherein said enclosure means and coating material are polyurethane.

10. The automatic implantable cardioverter/defibrillator system of claim 9 wherein the outer pore size of said polyurethane material is less than or equal to 20 microns and the thickness is from about 10 to 100 mils.

11. The automatic implantable cardioverter/defibrillator system of claim 1 wherein said porous bio-compatable enclosure means is a multi-layer composite.

12. A means for isolating an implantable electrically active probe including an electrode means of desired configuration and an insulated conductor attached to said electrode means for chronic tissue contact comprising:
    covering means for isolating said probe in a manner which substantially covers the probe except for said conductor, said covering means substantially consisting of a porous, bio-compatible material which allows infiltration of bodily fluids to provide a conductive path from said electrode member to the adjacent tissue yet has a thickness that determines the minimum spacing of said probe from direct contact with adjacent tissue and substantially isolates said electrode member from ingrowth of tissue in the manner of a dissection plane.

13. The apparatus of claim 12 wherein said porous biocompatible material has an average outer pore size less than or equal to 20 microns.

14. The apparatus of claim 12 wherein said covering means has a thickness of from about 10 mils to 100 mils.

15. The apparatus of claim 12 wherein said covering means further comprises a porous coating.

16. The apparatus of claim 15 wherein said porous biocompatible compatible material is of a non-abrasive texture and has a soft resiliency which reduces irritation to adjacent tissue due to repeated tissue impact and rubbing.

17. The apparatus of claim 12 wherein said porous biocompatible compatible material is an enclosing pouch.

18. The apparatus of claim 17 wherein said pouch consists essentially of polyurethane foam which has an outer average pore size less than or equal to 20 microns and is of a thickness of from 10 mils to 100 mils.

19. The apparatus of claim 18 wherein said porous biocompatible compatible material has a composite structure.

20. The apparatus of claim 12 further comprising an amount of immobilized medication in or beneath said covering means.

21. A means for isolating implantable devices of desired configuration associated with an electrically active probe including insulating conductor lead devices attached to an electrode member for chronic tissue contact comprising:

covering means for isolating the device in a manner which substantially covers the desired parts of a device, said covering means substantially consisting of a porous, biocompatible material which allows a degree of infiltration of bodily fluids to provide a conductive path including the electrode member which substantially isolates the covered part of the device from ingrowth of tissue in the manner of a dissection plane.

22. The apparatus of claim 21 wherein said porous biocompatible material has an average outer pore size less than or equal to 20 microns.

23. The apparatus of claim 22 wherein said covering means has a thickness of from about 10 mils to 100 mils.

24. The apparatus of claim 23 wherein said covering means further comprises a porous coating.

25. The apparatus of claim 21 wherein said porous biocompatible material is a shaped enclosed pouch.

26. The apparatus of claim 25 wherein said pouch consists essentially of polyurethane foam which has an outer average pore size less than or equal to 20 microns and is of a thickness of from 10 mils to 100 mils.

27. The apparatus of claim 26 wherein said porous biocompatible material has a composite structure.

28. The apparatus of claim 26 further comprising an amount of immobilized medication in or beneath said covering means.

29. A method of isolating an implantable electrically conductive device in juxtaposed relation to internal tissue of a patient comprising the steps of:

isolating the device by enveloping it in a flexible porous membrane said membrane being characterized by pores which are sufficiently permeable to body fluids at the site of installation such that the desired electrical conduction is established across said porous membrane via said bodily fluids but which pores are small enough to achieve a dissection plane.

30. The method of claim 29 wherein the electrically conductive device is an electrical stimulator device and comprising the further step of adjusting the thickness of the membrane to achieve the desired current density at the interface with the adjacent tissue at the maximum electrical stimulation of the device.

31. The method of claim 30 including the step of including an amount of immobilized medication beneath said membrane.

32. A method of installing an implantable electrically active probe in juxtaposed relation to internal tissue of a patient comprising the steps of:

providing a flexible porous membrane pouch for isolating the electrically active portion of the probe, said pouch being characterized by pores which are sufficiently permeable to body fluids such that the desired electrical conduction is established across said porous membrane via said bodily fluids but which pores are small enough to form a dissection plane to substantially prevent tissue ingrowth;

installing said pouch in place by fixing said pouch to tissue juxtaposed the desired probe location; and installing the electrically active probe by insertion into said pouch.

33. The method of claim 32 wherein said pouch is fixed in place by using a post and retainer arrangement in which the body tissue to which the pouch is to be attached is trapped between post members attached to the pouch and retainer members.

34. The method of claim 32 wherein said probe is inserted in a configuration other than that of its final disposition.

* * * * *

UNITED STATES PATENT AND TRADEMARK OFFICE
CERTIFICATE OF CORRECTION

PATENT NO. : 5,090,422

DATED : February 25, 1992

INVENTOR(S) : Roger W. Dahl et al

It is certified that error appears in the above-identified patent and that said Letters Patent is hereby corrected as shown below:

In column 10, line 60, after "biocompatable", delete "compatible".

In column 10, line 65, after "biocompatible", delete "compatible".

In column 11, line 4, after "biocompatible", delete "compatible".

In column 11, line 11, delete "insulating" and insert -- insulated.

Signed and Sealed this

First Day of June, 1993

Attest:

MICHAEL K. KIRK

Attesting Officer

Acting Commissioner of Patents and Trademarks